US00PP12419P2

(12) United States Plant Patent
Zaiger et al.

(10) Patent No.: US PP12,419 P2
(45) Date of Patent: Feb. 26, 2002

(54) PEACH TREE NAMED 'SPRING TREAT'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 17 days.

(21) Appl. No.: 09/771,707

(22) Filed: Jan. 30, 2001

(51) Int. Cl.[7] ..... A01H 5/00

(52) U.S. Cl. ..... Plt./197
(58) Field of Search ..... Plt./197

*Primary Examiner*—Bruce R. Campell
*Assistant Examiner*—Anne Marie Grüberg

(57) ABSTRACT

A new and distinct variety of peach tree (*Prunus persica*); the features of the tree and its fruit are characterized by the tree budded on Nemaguard (non-patented) rootstock, which is the primary rootstock used for peaches in California. The new peach tree was grown on Handford sandy loam soil with Storie Index rating 95, in the USDA hardiness Zone 9, near Modesto, Calif., with standard commerical fruit growing practices, such as pruning, thinning, spraying, irrigation and fertilization. Its novelty consists of the following combination of features that are desirable in a new variety:

1. Fruit having firm flesh with good storage and shipping quality.
2. Early maturity of medium to large size fruit with good flavor and eating quality.
3. Fruit having a high degree of attractive red skin color.
4. Regular and heavy production of fruit.
5. The tree having the ability to produce commercially quality fruit in areas with only 250 to 300 winter chilling hours.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach and nectarine trees, which are known to us, and mentioned herein, are May Crest Peach (U.S. Plant Pat. No. 4,064), Early Sungrand Nectarine (U.S. Plant Pat. No. 1,420), May Grand Nectarine (U.S. Plant Pat. No. 2,794), Tasty Gold Nectarine (U.S. Plant Pat. No. 5,623) Desert Gold Peach (unpatented), and Sam Houston Peach (unpatented).

ORIGIN OF VARIETY

The present new variety of peach tree (*Prunus persica*) was originated in our experimental orchard located near Modesto, Calif. as a first generation cross between two selected seedlings with the field identification numbers 78EC404 and 65EC70. The maternal parent 78EC404 originated from the selected peach seedlings 27GA914 crossed with May Crest Peach (U.S. Plant 4,064). The selected seedling 27GA 914 originated from a cross of an open pollinated seedling selection of Early Sungrand Nectarine (U.S. Plant Pat. No. 1,420) crossed with Desert Gold Peach (non-patented). The paternal parent (65EC70) also originated from a cross between two selected seedlings with the field identification numbers 34GA1155 and 36EB346. The seedling 34GA1155 was a cross between a selected seedling from a May Grand Nectarine (U.S. Plant Pat. No. 2,794)

cross with a peach of unknown parentage. This selection was then crossed with an open pollinated seedling of Sam Houston Peach (non-patented). The seedling 36EB346 originated from a first generation cross of Tasty Gold Nectarine (U.S. Plant Pat. No. 5,623) crossed with May Crest Peach (U.S. Plant Pat. No. 4,064). We planted and maintained under close observation a large number of these first generation seedlings growing on their own root, during which time we recongnized the desirable fruit characteristics of one low chilling seedling, which is the present variety and, in 1990, selected it for asexual propagation and commercialization.

ASEXUAL REPRODUCTION OF THE VARIETY

Asexual reproduction of the new and distinct variety of peach tree was by budding to Nemaguard rootstock (non-patented), a standard rootstock for peaches in California as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present invention relates to a new low chilling peach tree which produces quality commercial fruit in areas with 250 to 300 hours of winter chilling at or below 45° F., most commercially successful peach varieties grown in California must be grown in areas with colder winter climates. The present peach tree is of large size, vigorous, upright growth and a productive and regular bearer of medium to large, early maturing, yellow flesh, clingstone fruit with good flavor and eating quality. The fruit is further characterized by having good handling and shipping quality, having a high degree of attractive red skin color and in comparsion to the low chilling Desert Gold Peach (non-patented), the fruit of the new variety is larger in size, has firmer flesh with greater storage and shipping quality, a higher degree of attractive red skin color, greater production of commercial quality fruit and maturing in the same maturity season.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large, pruned to 12 to 14 feet in height and width, primarily for economical harvesting of fruit.

*Vigor.*—Vigorous, grows to a height of 6 to 7 feet the first growing season, growth varies with type of soil, cultural practices and climatic conditions.

*Growth.*—Upright, tendency to spread when tree starts producing heavy crop load.

*Productivity.*—Productive, normal fruit set is 1½ or more times the desired amount of fruit. Thinning and spacing of fruit is necessary.

*Form.*—Pruned to vase shape.

*Bearer.*—Regular, has set adequate fruit 6 consecutive years. No alternate bearing observed.

*Hardiness.*—Tree grown in hardiness Zone 9. Winter chilling requirement is 250 to 300 hours at or below 45° F.

*Density.*—Medium, usually pruned to vase shape allowing more sunlight to center of tree.

Trunk:

*Size.*—Medium to large. Average circumference 14 inches at 17 inches above ground on 5-year-old tree, varies with soil type, climatic conditions and cultural practices.

*Texture.*—Medium shaggy, as tree grows older, small areas of bark project outward creating a rough or shaggy condition.

*Color.*—Soot brown to hair brown (5-E-4) to (5-F-5).

Branches:

*Size.*—Medium. Average circumference of 8½ inches at 36 inches from ground. Average crotch angle approximately 38 degrees.

*Surface.*—Smooth to medium rough, roughness increases with age of branch.

*Lenticels.*—*Size — medium to large. Average number* 21 within 4 square inch surface. Average length — 5/32 inch. Average width —3/64 inch. Color — brownish orange to light brown (5-C-5) to (5-D-5). Varies with age of branch.

*Color.*—One year old wood — light green to light tan (3-D-6) to (4-C-8), mature wood varies from light brown to brown (5-D-5) to (5-E-6).

Leaves:

*Size.*—Large. Average length — 5 5/16 inches. Average width — 1 17/32 inches.

*Form.*—Lanceolate.

*Apex.*—Acuminate.

*Base.*—Cuneate.

*Margin.*—Serrate.

*Thickness.*—Medium.

*Surface.*—Upper surface — smooth. Lower surface — relatively smooth except for ridging of mid-rib, pinnate venation.

*Petiole.*—Average length — 3/8 inch. Average width — 1/16 inch. Grooved longitudinally. Color — light green to grayish green (1-D-5) to (1-D-7).

*Glands.*—Reniform, varies from 1 to 5. Average length — 3/64 inch. Average width — 1/32. Color — olive yellow (2-D-7) to Pompeian red (9-C-7). Color varies with maturity and exposure to sunlight. Location — on upper portion of petiole and base of leaf blade.

*Color.*—Upper surface — green to deep green (28-E-5) to (28-E-8). Lower surface — dull green to grayish green (28-D-4) to (28-D-7).

Flower buds:

*Size.*—Medium. Average length — 14/25 inch. Average width — 3/8 inch, three days before bloom.

*Hardiness.*—Hardy, with respect to central California winters.

*Form.*—Plump, conical, free, becoming elongated as flower bud matures.

*Pubescence.*—Pubescent.

*Shape.*—Obtuse.

*Color.*—Pink to rose pink (10-A-4) to (11-A-4).

Flowers:

*Size.*—Medium, non-showy. Average height — 37/64 inch. Average diameter — 1 inch.

*Petals.*—Number — five, alternately arranged to sepals. Shape — obovate, outer edges vary from smooth to slightly scalloped, narrows at point of attachment. Average length 15/32 inch. Average width 9/32 inch. Color — pale pink to rose pink (11-A-3) to (11-A-5), fades with age of flower.

*Sepals.*—Number — 5. Alternately arranged with petals. Color — lower surface varies from yellowish green to Reseda green (2-E-6) to (2-E-8). Upper surface varies from Reseda green to olive green (2-E-6) to (2-F-6). Average length 7/32 inch. Average width 5/32 inch at point of attachment.

*Stamens.*—Number varies from 22 to 26. Average length — 11/32 inch. Filament color — white to cream (1-A-1) to (2-A-5). Anther color — crayfish red to lake red (9-B-8) to (9-C-8).

*Pollen.*—Abundant, self-fertile.

*Pistil.*—Usually one. Average length —15/32 inch. Stigma slightly below stamens. Color — yellowish white to pastel yellow (1-A-2) to (1-A-4).

*Fragrance.*—Very slight.

*Blooming period.*—Early compared to other standard commercial peach varieties. Date of First Bloom: Feb. 14, 2000. Date of Last Bloom: Feb. 24, 2000. Varies slightly with climatic conditions.

*Color.*—Pale pink to rose pink (11-A-3) to (11-A-5), fades with age of flower.

Fruit:

*Maturity when described.*—Firm ripe.

*Date of first picking.*—May 22, 2000.

*Date of last picking.*—May 26, 2000. Varies slightly with climatic conditions.

*Size.*—Medium to large for early maturity. Average diameter axially — 2⅜ to 2½ inches. Average transversely in suture plane — 2½ to 2⅝ inches. Average weight — 161.9 grams. Average weight varies slightly with fertility of the soil, amount of thinning and climatic conditions.

*Form.*—Nearly globose, slightly elongated in suture plane.

*Suture.*—Shallow, extends from base to apex.

*Ventral surface.*—Rounded, nearly smooth, only very slightly lipped.

*Apex.*—Usually rounded, some fruit slightly retuse.

*Base.*—Retuse.

*Cavity.*—Rounded, slightly elongated in suture plane. Average depth — ½ inch. Average breadth — 1 inch.

Flesh:

*Ripens.*—Evenly.

*Texture.*—Firm, meaty.

*Fibers.*—Very few, small, tender.

*Aroma.*—Slight.

*Amydgalin.*—Undetected.

*Eating quality.*—Good.

*Flavor.*—Good, with good balance between sugar and acid.

*Juice.*—Moderate amount, enhances flavor.

*Brix.*—11.5°, varies with crop load and climatic conditions.

*Color.*—Varies from light yellow to butter yellow (4-A-4) to (4-A-5). Pit cavity varies from butter yellow to amber yellow (4-A-5) to (4-B-6).

Stem:

*Size.*—Average length — ⅜ inch. Average diameter — ⅛ inch, enlarged at point of fruit attachment.

*Color.*—Olive gray to olive yellow (2-D-5) to (2-D-6).

Skin:

*Thickness.*—Medium.

*Texture.*—Medium, tenacious to flesh.

*Tendency to crack.*—None.

*Color.*—Maize yellow to sunflower yellow (4-A-6) to (4-A-7) ground color, nearly overspread with reddish brown to garnet red (9-D-6) to (9-D-8).

*Astringency.*—None.

Stone:

*Type.*—Clingstone.

*Size.*—Large. Average length — 1⅜ inches. Average width — 1 inch. Average thickness — ¾ inch.

*Form.*—Obovoid.

*Base.*—Varies from rounded to straight.

*Apex.*—Acuminate. Length — short, approximately ⅛ inch.

*Surface.*—Irregularly furrowed toward apex, pitted toward base, pit cavities vary from round to elongated. Two sharp ridges on each side of suture extending from base to apex.

*Sides.*—Usually equal, some stones slightly unequal with one side extending further outward from suture plane.

*Tendency to split.*—Very slight.

*Color.*—Light tan to light brown when dry (5-C-6) to (5-C-8).

Use: Dessert. Market — local and long distance.

Keeping quality: Good, fruit hold firm in color storage for 2 weeks at 38 to 42° F. without internal breakdown of flesh or appreciable loss of eating quality.

Shipping quality: Good, picking and packing gave minimal bruising of flesh or scarring of fruit.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its low winter requirement of 250 to 300 hours, its ability to produce commercially quality fruit in areas with less winter chilling than most commercially successful varieties, which is of large size, vigorous upright growth; being a productive and regular bearer of medium to large, clingstone fruit with good flavor and eating quality; the fruit is further characterized by having a high degree of attractive red skin color and firm flesh with good storage and shipping quality.

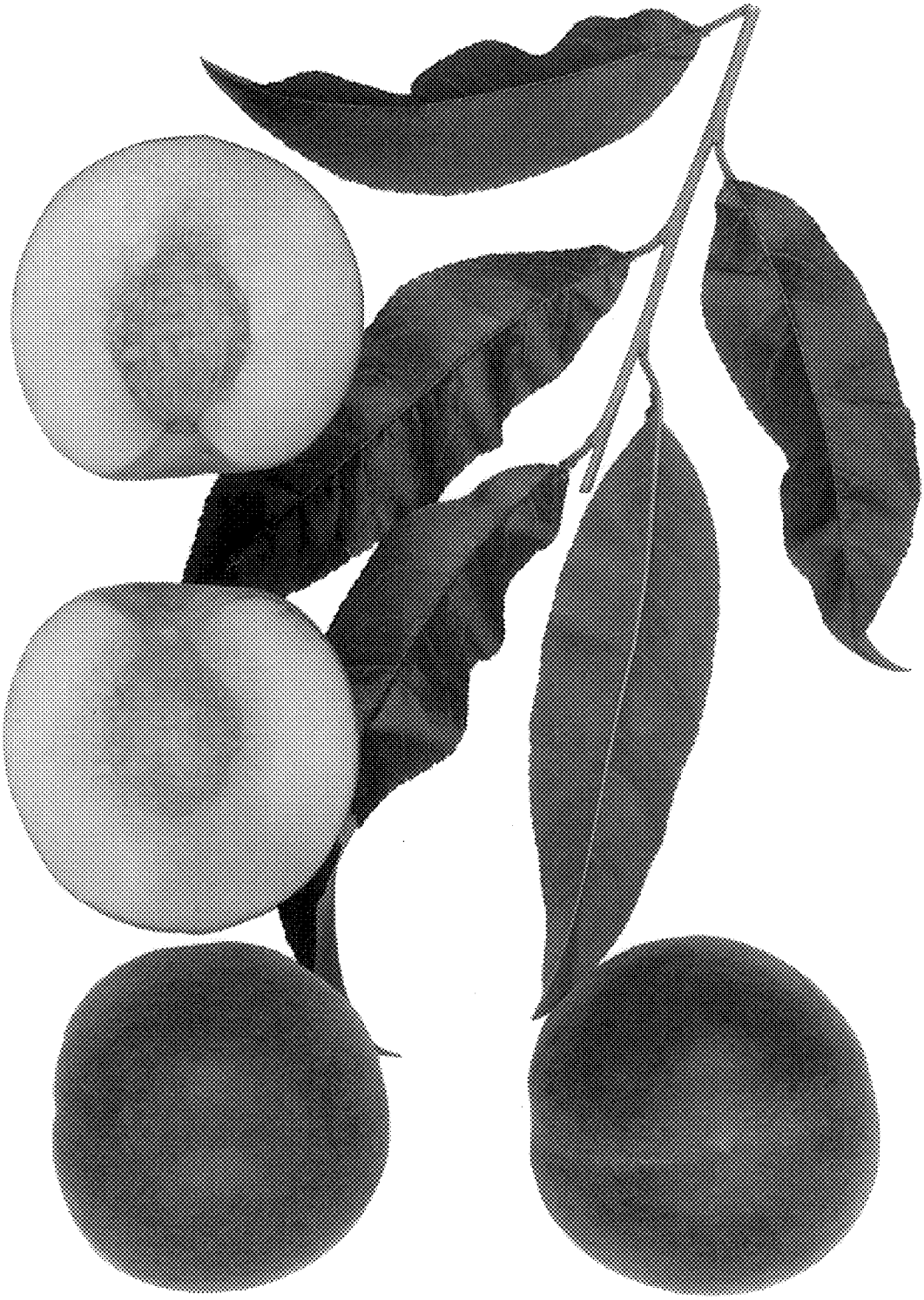

* * * * *